US011111258B2

United States Patent
Lin et al.

(10) Patent No.: US 11,111,258 B2
(45) Date of Patent: Sep. 7, 2021

(54) 3,3,3',3'-TETRAMETHYL-1,1'-SPIROBIINDANE-BASED PHOSPHINOOXAZOLINE LIGAND COMPOUND, PREPARATION METHOD AND USES OF THE SAME

(71) Applicant: ZHEJIANG UNIVERSITY, Hangzhou (CN)

(72) Inventors: Xufeng Lin, Hangzhou (CN); Weiye Sun, Hangzhou (CN); Haorui Gu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/959,672

(22) PCT Filed: Jan. 8, 2018

(86) PCT No.: PCT/CN2018/071714
§ 371 (c)(1),
(2) Date: Jul. 1, 2020

(87) PCT Pub. No.: WO2019/134158
PCT Pub. Date: Jul. 11, 2019

(65) Prior Publication Data
US 2021/0079030 A1 Mar. 18, 2021

(30) Foreign Application Priority Data
Jan. 3, 2018 (CN) .......................... 201810005764.8

(51) Int. Cl.
*C07F 9/653* (2006.01)
*B01J 31/24* (2006.01)
(52) U.S. Cl.
CPC ............. *C07F 9/653* (2013.01); *B01J 31/249* (2013.01); *B01J 2531/16* (2013.01); *B01J 2531/847* (2013.01)
(58) Field of Classification Search
CPC ..................................................... C07F 9/653
See application file for complete search history.

(56) References Cited

U.S. PATENT DOCUMENTS 5,516,944 A    5/1996    Hoffmann La Roche

FOREIGN PATENT DOCUMENTS

CN    1884290 A    12/2006
CN    101565434 A    10/2009

OTHER PUBLICATIONS

International Search Report (PCT/CN2018/071714 ); dated Sep. 4, 2018.

*Primary Examiner* — Joseph R Kosack
(74) *Attorney, Agent, or Firm* — W&G Law Group LLP

(57) ABSTRACT

The invention discloses a tetramethyl-7,7'-spirobiindane-based phosphinooxazoline ligand compound and its preparation method and use. The phosphinooxazoline ligand compound is a compound having a structure shown in general formula I or an enantiomer, a raceme or a diastereoisomer thereof. The phosphinooxazoline ligand obtained through a series of reaction steps using cheap and easily available 3,3,3',3'-tetramethyl-1,1'-spirobiindane-6,6'-diol as a starting material. The novel phosphinooxazoline ligand developed in the invention can be used to organic catalytic reactions, especially as a chiral phosphinooxazoline ligand widely used in metal-asymmetric catalytic reactions, having economical practicality and industrial application prospects.

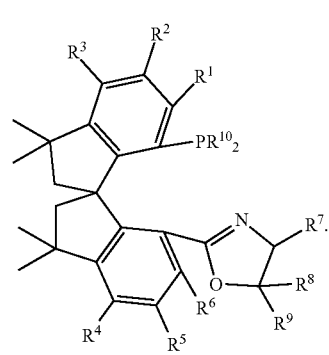

3 Claims, 1 Drawing Sheet

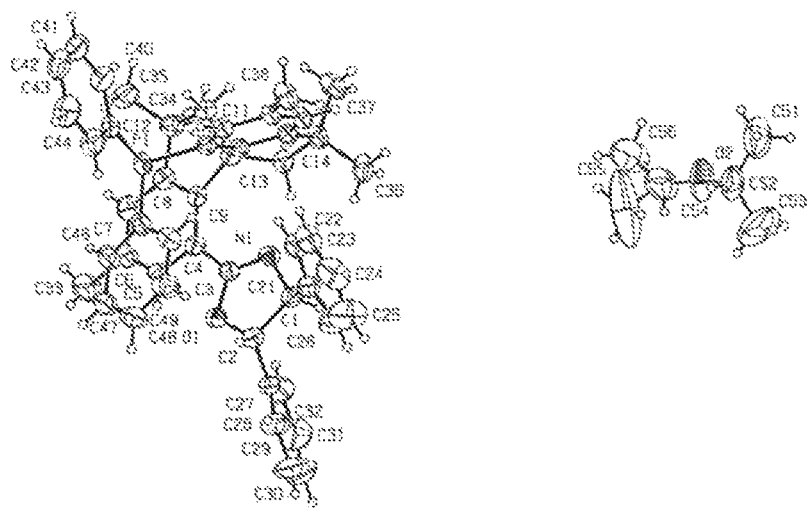

3,3,3',3'-TETRAMETHYL-1,1'-SPIROBIINDANE-BASED PHOSPHINOOXAZOLINE LIGAND COMPOUND, PREPARATION METHOD AND USES OF THE SAME

CROSS-REFERENCE TO RELATED APPLICATIONS

This application is based on International Application No. PCT/CN2018/071714 filed on Jan. 8, 2018, which claims priority to Chinese Patent Application No. 201810005764.8, filed on Jan. 3, 2018 and titled with "3,3,3',3'-TETRAMETHYL-1,1'-SPIROBIINDANE-BASED PHOSPHINOOXAZOLINE LIGAND COMPOUND, PREPARATION METHOD AND USES OF THE SAME", the content of which is incorporated herein by reference in their entireties.

TECHNICAL FIELD

The invention relates to the technical field of organic synthetic chemistry, and relates to a novel 3,3,3',3'-tetramethyl-1,1'-spirobiindane-based phosphinooxazoline ligand compound, a preparation method and a use thereof. Such a ligand can be used in a metal-catalyzed coupling reaction and an asymmetric reaction.

BACKGROUND

Asymmetric catalytic synthesis is one of the most intensive research areas in modern synthetic chemistry. This technique is one of the most direct and effective chemical methods for obtaining chiral compounds. It has advantages such as chiral proliferation, high enantio-selectivity, economy, and ease industrialization. It is challenging in the field of synthetic chemistry to perform efficient and highly selective asymmetric catalytic reactions, and one of the pivotal scientific issues thereof is to develop or discover new and efficient chiral ligands and their catalysts. The design and synthesis of chiral ligands have been advancing rapidly, many excellent chiral phosphinooxazoline ligands based on various skeletons, as shown below, have been synthesized, and some of them have been applied in the industrial production. However, the chiral ligands are not for all-purpose due to the existing problems such as limited application scopes for the ligands and high dependence on reaction substrates. It is urgent for the catalytic asymmetric synthesis reactions to seek for chiral ligands having new skeletons.

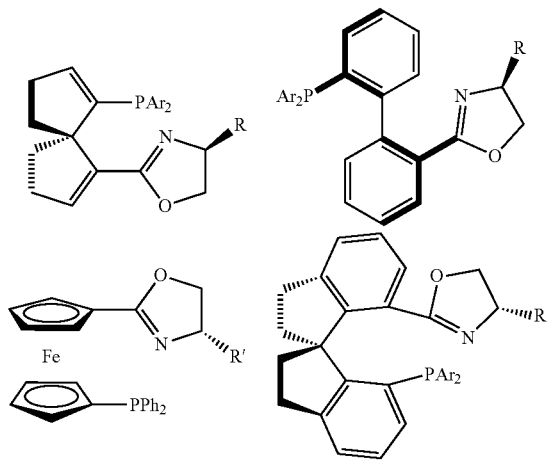

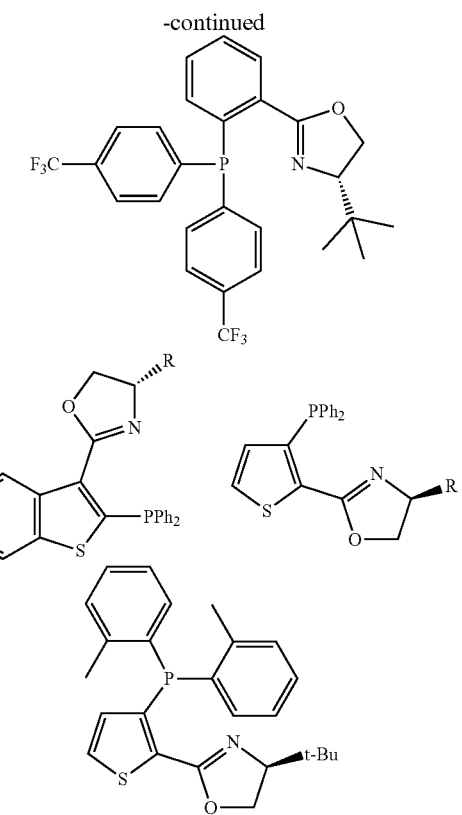

The design and synthesis of the chiral ligands, including the improvement of catalytic activity and enantio-selectivity, mainly consider electrical and structural factors such as dihedral angle, steric hindrance, and skeleton rigidity etc. Currently, it is generally believed that a dihedral angle has a great influence on asymmetric catalytic enantio-selectivity (for example, Acc. Chem. Res. 2007, 40, 1385-1393; Tetrahedron: Asymmetry 15 (2004) 2185-2188; J. Org. Chem. 1999, 65, 6223).

In 1999, Birman et al. synthesized racemic 1,1'-spirobiindane-7,7'-diol (SPINOL) through a six-step reaction starting from m-methoxybenzaldehyde, and obtained the corresponding optical enantiomer by chemical resolution (Tetrahedron: Asymmetry 1999, 10, 12). However, corresponding 3,3,3',3'-tetramethyl-1,1'-spirobiindane-7,7'-diol cannot be obtained according to this scheme or other published methods. In 2003, ZHOU Qilin et al. prepared 7,7'-spirobiindane-based phosphinooxazoline ligand (SIPHOX) through a seven-step reaction using the optically active 1,1'-spirobiindane-7,7'-diol (SPINOL) as raw material (CN101565434, CN100432083), and the ligand has been successfully applied in the asymmetric catalytic reaction. However, starting from the industrially available raw material m-methoxybenzaldehyde, at least 13 steps of synthesis reactions and one step of chiral resolution are required to obtain the corresponding SIPHOX, that is, the reaction steps were redundancy and the preparation cost was high, which affects the practicality to a certain extent. In addition, it is unable to obtain a phosphinooxazoline ligand, which has electron-withdrawing groups such as p-trifluoromethyl and 3,5-bis(trifluoromethyl) on the phenyl group of the phosphorus atom.

3,3,3',3'-tetramethyl-1,1'-spirobiindane-6,6'-diol (MSPINOL) can be obtained directly from industrialized bisphenol series products through acid catalysis with high yield, and a large scale method and a chiral resolution method are known (as shown in the figure, J. Chem. Soc., 1962, 415-418; Org. Lett., 2004, 6, 2341-2343; US 2006/0020150; U.S. Pat. No. 4,879,421; Bull. Chem. Soc. Japan, 1977, 44, 496-505; and Chinese patent application No. CN 201711330428.2). The corresponding raw material, bisphenol, is very cheap and can be obtained through a condensation reaction of acetone and phenol or its derivatives. There are many bisphenol series products on large sales in the industry, such as bisphenol A, bisphenol C, etc., for example, the annually produced and sold bisphenol A in the world are as high as more than 3 million tons, with a price less than 10,000 RMB per ton. The present application employs the cheap and easily available 3,3,3',3'-tetramethyl-1,1'-spirobiindane-6,6'-diol to design and prepare the corresponding tetramethyl-7,7'-spirobiindane-based phosphinooxazoline ligand (MSI-PHOX). Such a kind of ligands has no active aryl methylene group on the spiro ring skeleton, the 3,3,3',3'-tetramethyl-1,1'-spirobiindane skeleton is more stable and has stronger rigidity, the raw materials thereof are cheap and abundant, the synthesis scheme is shorter, the preparation cost is low, the practicability is high, and the unique dihedral angle indicates different catalytic effects or uses. In particular, it is possible in the present application to obtain the phosphinooxazoline ligand that has an electron-withdrawing group such as trifluoromethyl, 3,5-bis(trifluoromethyl), and other substituents on the phenyl group of the phosphorus atom, which will greatly enrich the chiral spiro phosphinooxazoline ligands. Based on the method disclosed in the present application, the 3,3,3',3'-tetramethyl-1,1'-spirobiindane-based phosphinooxazoline ligands are generally prepared through a synthesis reaction scheme only including the following 9 steps, and ligands having different structures can be prepared from tetramethyl spiro dibromide. The tetramethyl spiro dibromide and its derivatives or its enantiomer can be prepared according to the published literature (Chinese patent application No. CN 201711330428.2).

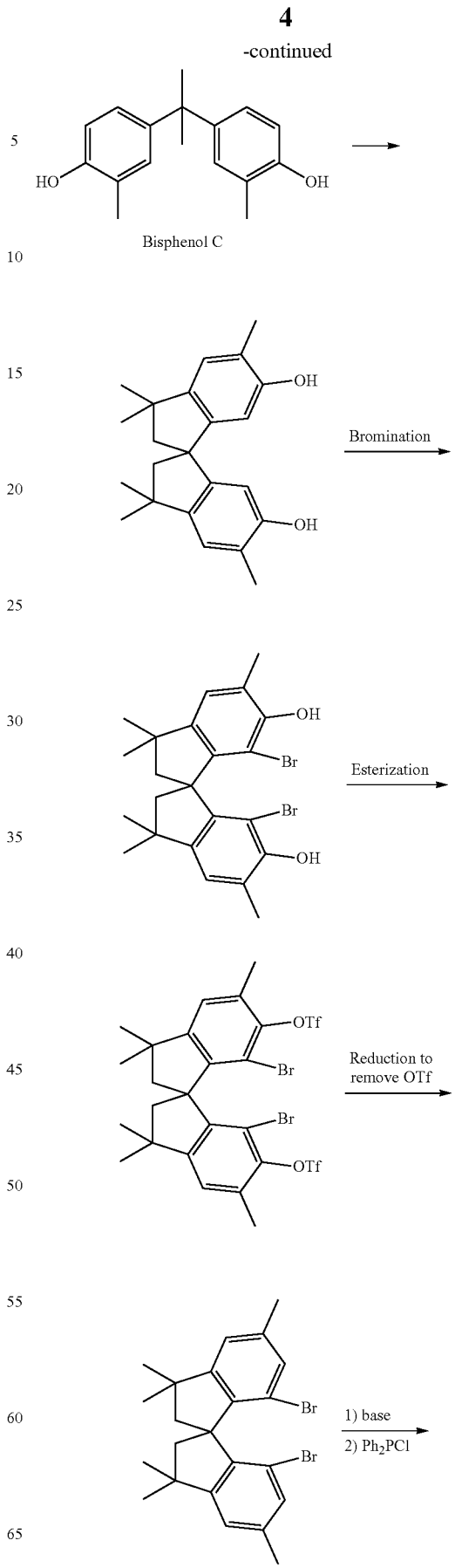

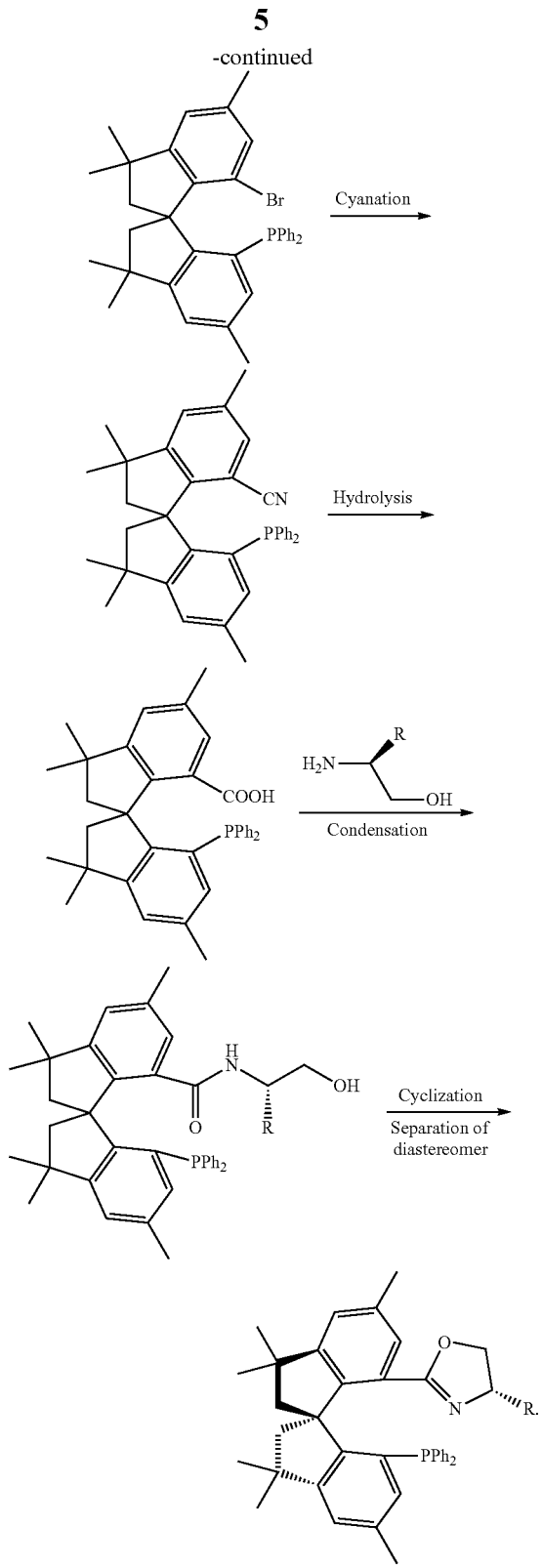

A 3,3,3',3'-tetramethyl-1,1'-spirobiindane-based phosphinooxazoline ligand is a compound represented by formula I, or a enantiomer, a raceme or a diastereoisomer thereof:

I wherein $R^1$ and $R^6$ are each independently selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted arylmethyleneoxy, unsubstituted or substituted heteroarylmethyleneoxy, unsubstituted or substituted aryl, and unsubstituted or substituted heteroaryl; $R^2$, $R^3$, $R^4$, and $R^5$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl; $R^7$ is selected from the group consisting of hydrogen, $C_1$-$C_{10}$ alkyl or perfluoroalkyl, $C_3$-$C_6$ cycloalkyl, adamantyl, $C_6$-$C_{14}$ aryl, arylmethylene, heteroarylmethylene, arylethyl, substituted aryl, $C_5$-$C_{14}$ heteroaryl, substituted heteroaryl, hydroxymethyl, alkylbenzoyloxymethylene, arylbenzoyloxymethylene, CH(Me)OH, CH(Me)OCOPh, $CMe_2OSiMe_3$, $CMe_2OBn$, $CH_2OSiMe_2{}^tBu$, $CH_2SMe$, $CH_2SPh$, $CH_2CH_2SMe$, $CMe_2SMe$, $CMe_2Ph$, $CMePh_2$, $CPh_3$, CH(Ph)OH, CH(Ph)OMe, CH(Ph)OBn, CH(Ph)OCOMe, CH(Ph)OCOPh, alkoxymethylene, and aryloxymethylene; $R^8$ and $R^9$ are each independently selected from the group consisting of hydrogen, $C_1$-$C_{10}$ alkyl or perfluoroalkyl, $C_3$-$C_6$ cycloalkyl, $C_6$-$C_{14}$ aryl, substituted aryl, $C_5$-$C_{14}$ heteroaryl, substituted heteroaryl, alkoxymethylene, aryloxymethylene, $CH_2OCHPh_2$, $CH_2OCPh_3$, and $CH_2OCH_2Ph$; and $R^{10}$ is selected from the group consisting of $C_1$-$C_{10}$ alkyl or perfluoroalkyl, $C_3$-$C_6$ cycloalkyl, $C_6$-$C_{14}$ aryl, substituted aryl, $C_5$-$C_4$ heteroaryl, and substituted heteroaryl, wherein $R^7$ and $R^8$ are capable of forming a ring structure or a benzo ring structure, and the substituted aryloxy, the substituted aryl, or the substituted heteroaryl contains one or more substituents each independently selected from the group consisting of halogen, hydroxyl, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, $C_6$-$C_{14}$ aryl, aryloxy, and heteroaryl; and the heteroaryl is $C_5$-$C_{14}$ heteroaryl.

Preferably, the 3,3,3',3'-tetramethyl-1,1'-spirobiindane-based phosphinooxazoline ligand represented by formula I is any one of the following compounds:

SUMMARY

Purposes of the present application are to provide a 3,3,3',3'-tetramethyl-1,1'-spirobiindane-based phosphinooxazoline ligand compound, a preparation method thereof, and a use thereof.

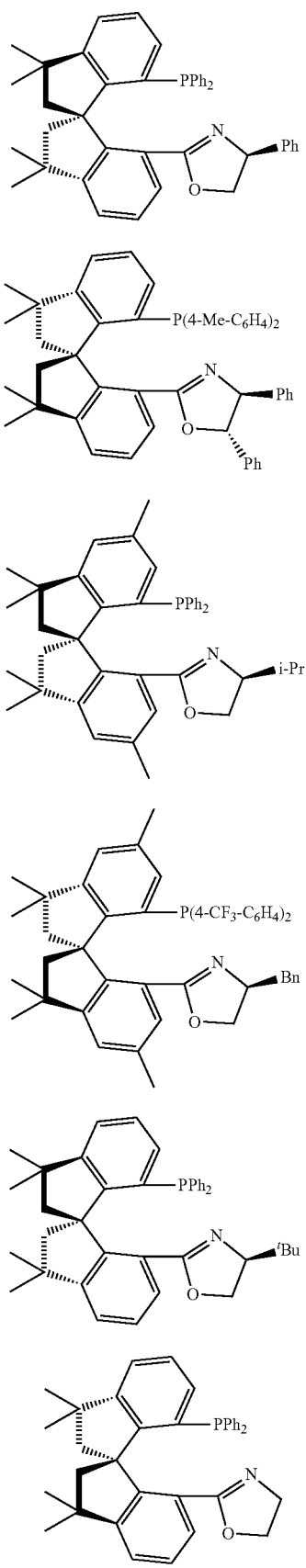

(R$_a$,S)-I-a

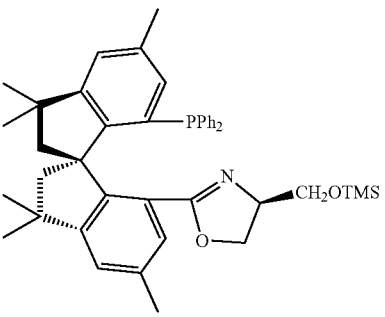

(S$_a$,S,S)-I-b (R$_a$,S)-I-c (S$_a$,S)-I-d (R$_a$,S)-I-e (S$_a$)-I-f (R$_a$,R)-I-g (S$_a$,S)-I-h

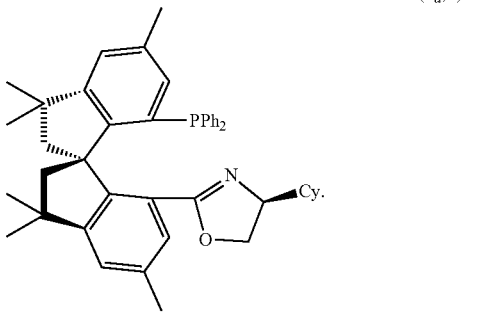

A preparation method for the compound I includes the following steps: preparing a compound represented by formula I through a mono-substitution reaction of a compound represented by formula II, as a starting material, with disubstituted phosphine halide under an effect of an alkali, subjecting the compound represented by formula III to a palladium-catalyzed cyanation, an acidic hydrolysis, and a condensation reaction with an aminoethanol compound to form amphenicol, and then conducting a cyclization reaction to obtain the compound represented formula I:

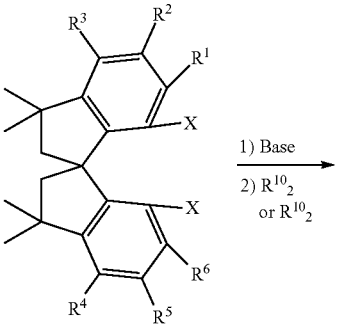

II

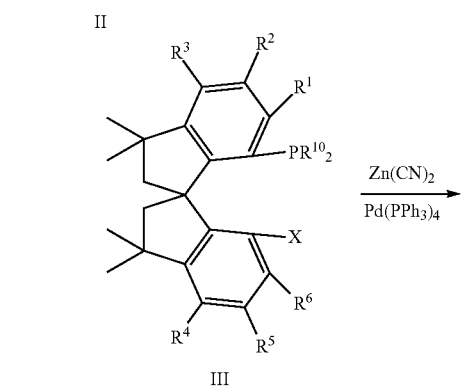

III

-continued

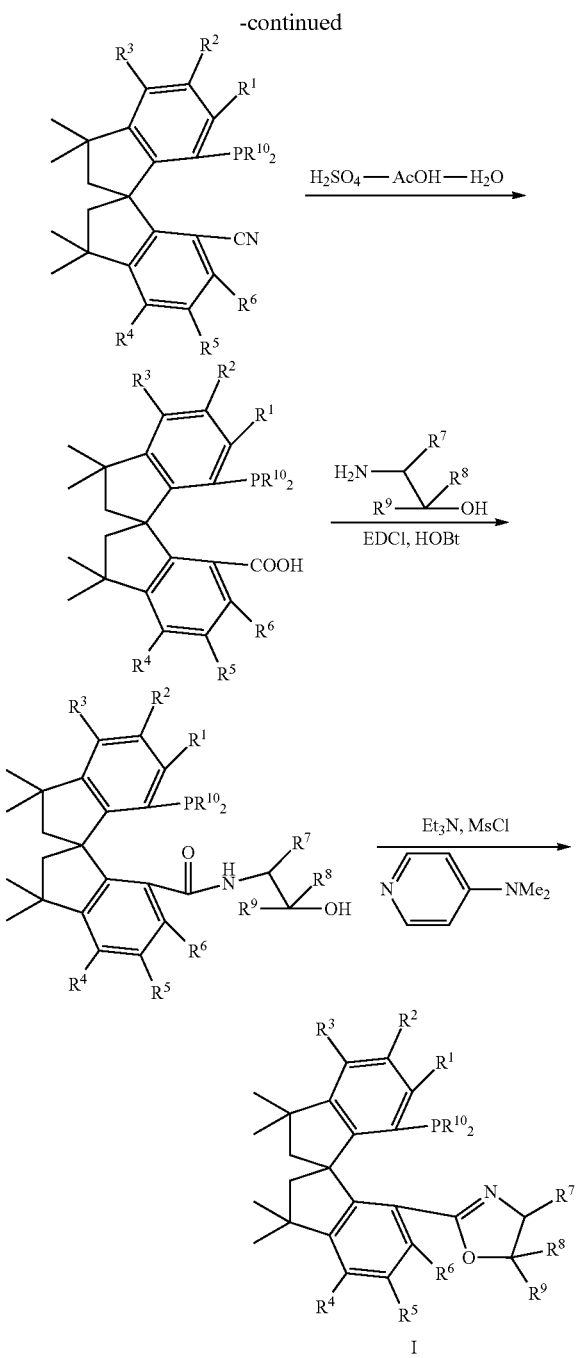

wherein $R^1$-$R^{10}$ in the formula I are the same as those defined in claim 1; X in the formula II is bromine or iodine; and in the formula II, $R^1$ and $R^6$ are each independently selected from the group consisting of hydrogen, hydroxyl, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, unsubstituted or substituted heteroaryl; $R^2$, $R^3$, $R^4$, $R^5$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, unsubstituted or substituted aryloxy, unsubstituted or substituted heteroaryloxy, unsubstituted or substituted aryl, and unsubstituted or substituted heteroaryl, wherein the substituted aryloxy, the substituted aryl, or the substituted heteroaryl contains one or more substituents each independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; and the heteroaryl$C_5$-$C_{14}$heteroaryl; and EDCI is 1-(3-dimethylaminopropyl)-3-ethylcarbodiimide hydrochloride, and HOBt is 1-hydroxylbenzotriazole.

A use of the phosphinooxazoline ligand of the present application includes that the phosphinooxazoline ligand is complexed with a metal salt of iron, gold, silver, copper, zinc, magnesium, rhodium, ruthenium, nickel, molybdenum, palladium, or cobalt, to prepare catalysts.

The phosphinooxazoline ligand is used in a metal-catalyzed coupling reaction or a metal-catalyzed asymmetric reaction, preferably in an asymmetric catalytic Friedel-Craft alkylation reaction or an asymmetric catalytic arylation reaction, either of which is catalyzed by metals.

The phosphinooxazoline ligand of the present application can be prepared through a series of reaction steps using cheap and easily available 3,3,3',3'-tetramethyl-1,1'-spirobi-indane-6,6'-diol as a starting material. The novel phosphinooxazoline ligand developed by this method can be used in organic catalytic reactions, especially as a chiral phosphinooxazoline ligand widely used in asymmetric metal-catalyzed reactions, having economic practicability and industrial application prospect.

It should be understood that within the scope of the present application, the technical features of the present application mentioned above and described in the following embodiments can be combined with each other to constitute new or preferred technical solutions, which will not be described in detail for brevity.

BRIEF DESCRIPTION OF DRAWINGS

FIG. 1 is an X-ray crystal diffraction pattern of a product in Example 5 of the present application.

DESCRIPTION OF EMBODIMENTS

The following examples are provided to facilitating the understanding of the present application, but are not intended to limit to the present application.

General reaction conditions are described as below: when using air-sensitive reagents, all reactions and controls are performed in a nitrogen-filled glove box or using standard Schlenk technology. The reaction solvents are dried by a general standard process.

Example 1

Synthesis of 3,3,5,3',3',5'-hexamethyl-7-bromo-7'-(diphenylphosphino)-1,1'-spirobiindane (III-b)

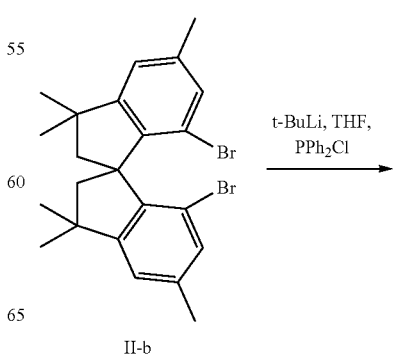

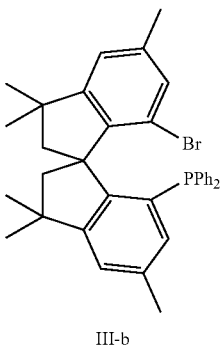

III-b

Under nitrogen atmosphere, II-b (1 g, 1.08 mmol) and 15 mL of degassed anhydrous tetrahydrofuran were added to a reaction flask. The temperature was lowered to −78° C. An n-hexane solution of tert-butyllithium (1 mL, 0.6M) was added. After three hours of reaction, diphenylphosphine chloride (2 mmol) was added. After 30 minutes, the temperature naturally was raised to room temperature, and the reaction continued for 6 hours. An appropriate amount of dilute hydrochloric acid was added to quench and finish the reaction. Extraction was performed with ethyl acetate. The organic phase was washed with saturated sodium chloride solution, dried over anhydrous sodium sulfate, and filtered with suction. The filtrate was concentrated, and purified with silica gel flash column chromatography (eluent:petroleum ether:ethyl acetate=50:1) to obtain III-b, with a yield of 50%; m.p. 212-213° C.; $^1$H NMR (400 MHz, CDCl$_3$) δ 7.23-7.14 (m, 6H), 7.07-6.99 (m, 4H), 6.97 (s, 1H), 6.87 (s, 1H), 6.72 (d, J=4.6 Hz, 1H), 6.64 (s, 1H), 2.76 (d, J=11.9 Hz, 1H), 2.55 (d, J=13.1 Hz, 1H), 2.31 (d, J=13.1 Hz, 1H), 2.24 (d, J=5.8 Hz, 7H), 1.42 (s, 3H), 1.37 (s, 3H), 1.35 (s, 3H), 1.28 (s, 3H).

Example 2

Synthesis of (R)-3,3,5,3',3',5'-hexamethyl-7-bromo-7'-(diphenylphosphino)-1,1'-spirobiindane

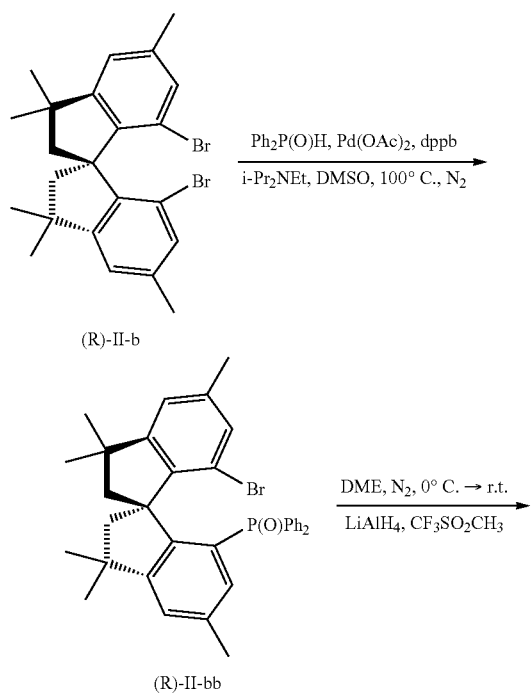

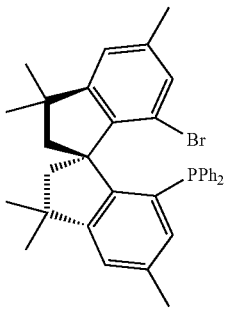

(R)-III-b

Under nitrogen atmosphere, (R)-II-b (4.62 g, 10 mmol), diphenylphosphine oxide (4.02 g, 20 mmol), palladium acetate (224.5 mg, 1 mmol), 1,4-bis(diphenylphosphino)butane (dppb, 426.5 mg, 2 mmol), and 40 mL of fully degassed dimethyl sulfoxide DMSO were added in a dried reaction flask, and stirred to mix thoroughly. N, N-diisopropylethylamine (7.0 mL, 40 mmol) was added and heated to 100° C., and reacted for 24 hours. TLC was used to monitor the reaction. The solution was cooled to room temperature, diluted with ethyl acetate, and washed with saturated brine. The organic phase was washed sequentially with 5% HCl solution, saturated NaHCO$_3$ solution, and saturated NaCl solution, dried over anhydrous Na$_2$SO$_4$, filtered to remove the solvent, and purified with flash chromatography on silica gel column (eluent: ethyl acetate/petroleum ether=1/4) to obtain 2.9 g of white solid product (R)-II-bb; m.p. 251-252° C.; H NMR (400 MHz, CDCl$_3$) δ 7.46-7.27 (m, 10H), 7.12 (s, 1H), 6.87 (s, 1H), 6.80 (d, J=15.0 Hz, 1H), 6.27 (s, 1H), 3.45 (d, J=12.2 Hz, 1H), 2.48 (d, J=13.1 Hz, 1H), 2.24 (dd, J=20.6, 10.4 Hz, 8H), 1.63 (s, 3H), 1.40 (s, 3H), 1.35 (s, 3H), 1.27 (s, 3H); HRMS (GC-TOF, EI): calcd for C$_{35}$H$_{36}$OPBr 582.1687, found 582.1672.

Under nitrogen atmosphere, (R)-II-bb (1.75 g, 3 mmol) and 20 mL of anhydrous ethylene glycol dimethyl ether (DME) were added to a reaction flask, and mixed under stirring. CF$_3$SO$_3$CH$_3$ (375p, 3.3 mmol) was added at room temperature, and then stirred and reacted at room temperature for 3 hours. Subsequently, the reaction flask was placed in an ice water bath, LiAlH$_4$ (3 ml, 7.5 mmol, 2.5 mol/L in THF) solution was slowly added dropwise, and then the mixture was naturally warmed to room temperature. Subsequently, the reaction was carried out at room temperature for 3 hours, and the reaction condition was monitored by using TLC. Then 1 M dilute HCl solution was slowly added dropwise in the ice bath to quench the reaction, followed by extraction with ethyl acetate. The organic phase was washed with saturated NaCl, dried over anhydrous Na$_2$SO$_4$, filtered to remove the solvent, and purified with silica gel flash column chromatography (eluent: ethyl acetate/petroleum ether=1/50) to obtain a white solid product (R)-III-b (1.6 g, yield 93%); $^{31}$P NMR (162 MHz, CDCl$_3$) δ −22.66; HRMS (GC-TOF): calcd for C$_{35}$H$_{36}$PBr 566.1738, found 566.1756.

Example 3

Synthesis of (R)-3,3,5,3',3',5'-hexamethyl-7-bromo-7'-(bis(3,5-bis(trifluoromethyl)phenyl)phosphino)-1,1'-spirobiindane ((R)-III-b)

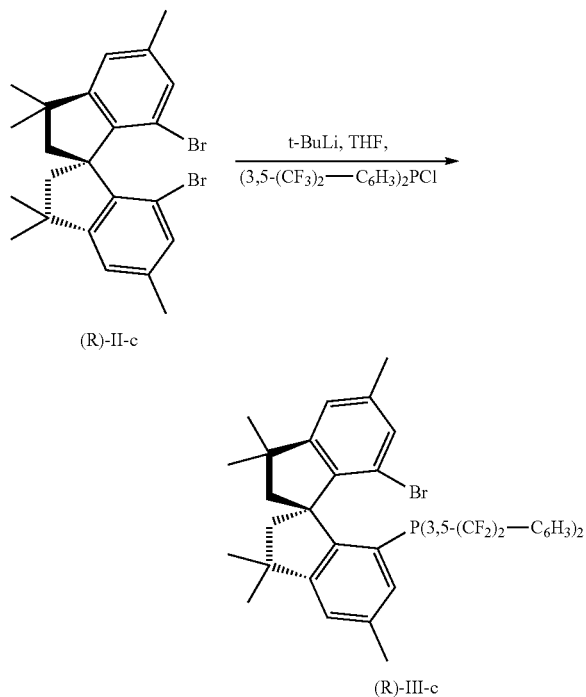

Under nitrogen atmosphere, (R)-II-b (1 mmol) and 15 mL of degassed anhydrous tetrahydrofuran were added into a reaction flask. The temperature was lowered to −78° C., and an n-hexane solution of t-butyllithium (1.1 mL, 1.6M) was added. After reacting for three hours, bis(3,5-bis(trifluoromethyl) phenyl)phosphine chloride (2 mmol) was added. The temperature naturally was raised to room temperature after 30 minutes, and the reaction continued for 6 hours. The reaction was quenched by adding an appropriate amount of dilute hydrochloric acid, followed by extracting with ethyl acetate. The organic phase was washed with saturated sodium chloride solution, dried over anhydrous sodium sulfate, and suction filtered. The filtrate was concentrated, and purified with silica gel flash column chromatography (eluent:petroleum ether:ethyl acetate=50:1) to obtain (R)-III-c, with a yield of 45%.

Example 4

Synthesis of 3,3,5,3',3',5'-hexamethyl-7'-(diphenylphosphino)-1,1'-spirobiindane-7-formic acid (V)

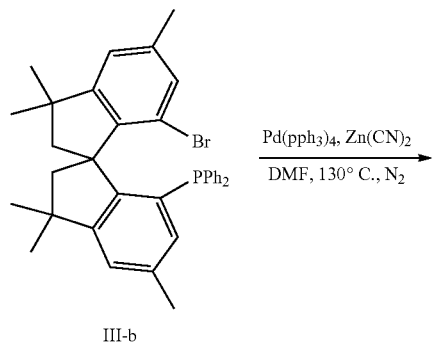

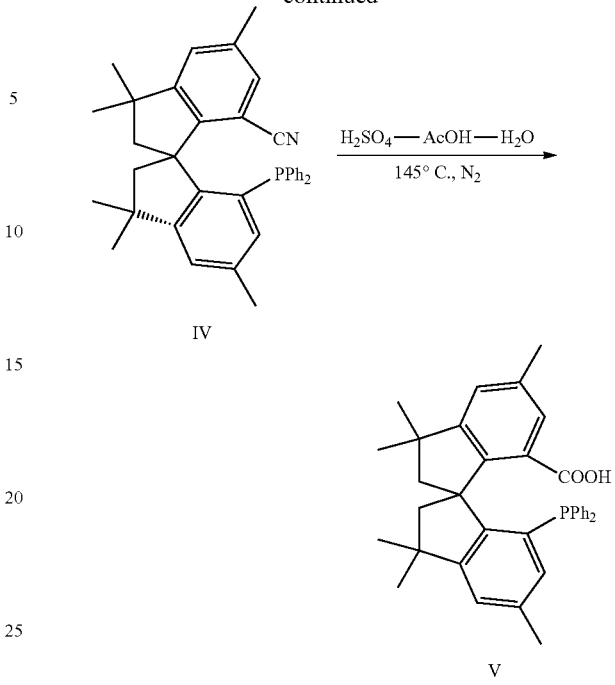

Under $N_2$ protection, III-b (2.84 g, 5 mmol), $Zn(CN)_2$ (645.7 mg, 5.5 mmol) and $Pd(PPh_3)$ (577.8 mg, 0.5 mmol) were added into a 100 mL three-necked flask. 50 mL of anhydrous DMF was added, and under stirring, the temperature was raised to about 130° C. The reaction condition was monitored by TLC, and the reaction was completed and stopped after 36 h. The reaction system was cooled to room temperature, diluted with ethyl acetate, washed sequentially with saturated $NaHCO_3$ and saturated NaCl, dried over anhydrous $Na_2SO_4$, and purified with silica gel column chromatography (eluent: ethyl acetate/petroleum ether=1/50) after removing the solvent through rotary evaporation to obtain a product of 3,3,5,3',3',5'-hexamethyl-7-cyano-7'-(diphenylphosphino)-1,1'-spirobiindane (IV), (1.67 g, yield 65%); m.p. 220-221° C.; $^1$H NMR (400 MHz, $CDCl_3$) δ 7.26 (dd, J=12.3, 4.6 Hz, 1H), 7.23-7.15 (m, 5H), 7.06 (s, 1H), 7.02 (s, 1H), 6.97 (td, J=9.2, 3.9 Hz, 4H), 6.69 (d, J=4.1 Hz, 1H), 6.41 (s, 1H), 3.06 (dd, J=13.1, 2.5 Hz, 1H), 2.44-2.39 (m, 1H), 2.36 (d, J=1.8 Hz, 2H), 2.23 (s, 3H), 2.20 (s, 3H), 1.55 (s, 3H), 1.47 (s, 3H), 1.36 (s, 3H), 1.29 (s, 3H).

Under $N_2$ protection, IV (1.03 g, 2 mmol) was added into a 100 mL three-necked flask, and then a degassed acid mixture solution of 10 ml $H_2SO_4$, 15 ml $H_2O$ and 5 ml AcOH was added. The system was warmed up to about 145° C., and reacted under reflux with stirring, and the reaction condition was monitored by TLC. After 48 h, the reaction was completed and stopped, the temperature was cooled to room temperature, followed by diluting and quenching with water under an ice bath. Extraction was performed three times with ethyl acetate. The organic phase was washed with saturated NaCl, dried over anhydrous $Na_2SO_4$, and purified with silica gel column chromatography (eluent: ethyl acetate/petroleum ether=1/10) after removing the solvent through rotary evaporation, so as to obtain a product V, 0.80 g, with a yield of 75%; m.p. 237-238° C.; $^1$H NMR (400 MHz, DMSO) δ 12.13 (s, 1H), 7.30 (d, J=6.5 Hz, 4H), 7.24-7.14 (m, 4H), 7.00-6.91 (m, 3H), 6.86 (dd, J=10.9, 4.1 Hz, 2H), 6.48 (d, J=4.0 Hz, 1H), 2.74 (d, J=12.3 Hz, 1H), 2.32 (s, 3H), 2.21 (s, 2H), 2.18-2.10 (m, 4H), 1.40 (s, 3H), 1.30 (s, 3H), 1.25 (s, 3H), 1.14 (s, 3H).

According to the above reaction process, the chiral compound (R)-3,3,5,3',3',5'-hexamethyl-7'-(diphenylphosphino)-1,1'-spirobiindane-7-formic acid ((R)-V) was obtained by using the chiral compound (R)-III-b instead of III-b, and a yield of the two steps achieved 55%.

Example 5

Synthesis of 3,3,5,3',3',5'-hexamethyl-7'-(diphenylphosphino)-1,1'-spirobiindane-7-oxazoline

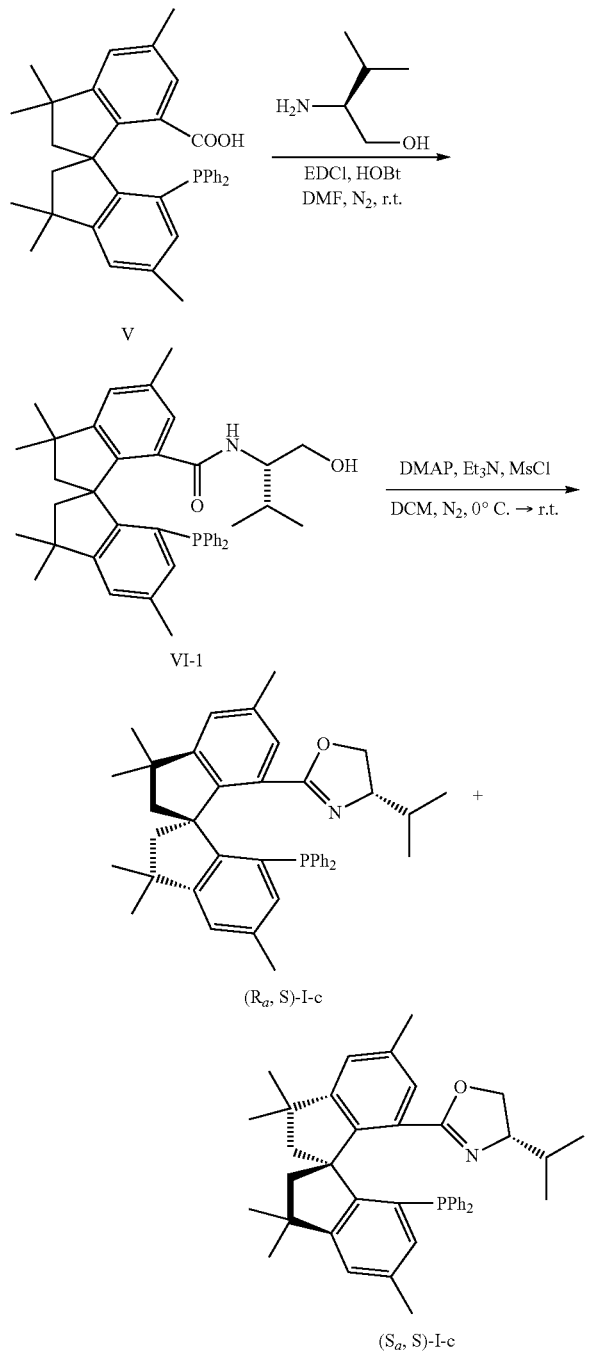

Under $N_2$ protection, V (266.3 mg, 0.5 mmol), L-valinol (154.7 mg, 1.5 mmol), EDCI (287.6 mg, 1.5 mmol), and HOBt (202.7 mg, 1.5 mmol) were added into a 50 mL three-necked flask. 20 mL of anhydrous N,N-dimethylformamide (DMF) was added at room temperature to react under stirring, and the reaction condition was monitored by TLC. After 24 h, the reaction was complete. The reaction was stopped and quenched with water, followed by extracting with ethyl acetate, washing with saturated NaCl, drying over anhydrous $Na_2SO_4$, and filtering. The solvent was then removed from the filtrate by rotary evaporation, and a product VI-1 was obtained and used directly in a next step of reaction.

Under $N_2$ protection, VI-1 (0.5 mmol) and DMAP (6.1 mg, 0.05 mmol, 4-N-dimethylaminopyridine) were added into a 50 mL three-necked flask. 15 mL of anhydrous $CH_2Cl_2$ was added and dissolved under stirring. Then, $Et_3N$ (555 μL, 4 mmol) and MsCl (155 μL, 2 mmol) were added sequentially in ice-water bath. Then, the system was naturally warmed to room temperature and stirred overnight. The reaction condition was tracked by TLC until the reaction was complete. The system was quenched with water, extracted with $CH_2Cl_2$, washed with saturated NaCl, and dried over anhydrous $Na_2SO_4$. After removing solvent by rotary evaporation, the silica gel column chromatography (eluent: ethyl acetate/petroleum ether=1/20) was used for separation to obtain a pair of diastereoisomers $(R_a, S)$-I-c (255 mg, with a yield of the two steps: 85%) and $(S_a, S)$-I-c (234 mg, with a yield of the two steps: 78%).

$(R_a, S)$-I-c: m.p. 199-200° C.; $[\alpha]_D^{20}$=+131 (c 0.1, $CH_2Cl_2$); $^1$H NMR (400 MHz, $CDCl_3$) δ 7.39 (s, 1H), 7.22 (dd, J=6.8, 3.4 Hz, 3H), 7.20-7.16 (m, 3H), 7.09 (td, J=7.0, 3.1 Hz, 2H), 7.04 (s, 1H), 6.98-6.92 (m, 3H), 6.57 (d, J=4.4 Hz, 1H), 3.79-3.68 (m, 1H), 3.41 (dd, J=17.7, 9.6 Hz, 1H), 2.84 (t, J=9.2 Hz, 2H), 2.39 (s, 3H), 2.28-2.07 (m, 6H), 1.41 (s, 3H), 1.29 (s, 6H), 1.16-1.06 (m, 4H), 0.89 (d, J=6.6 Hz, 3H), 0.56 (d, J=6.7 Hz, 3H);

$(S_a, S)$-I-c: m.p. 190-191° C.; $[\alpha]_D^{20}$=−182 (c 0.1, $CH_2Cl_2$); $^1$H NMR (400 MHz, $CDCl_3$) δ 7.47 (s, 1H), 7.22 (dd, J=4.0, 2.3 Hz, 3H), 7.17 (d, J=4.6 Hz, 3H), 7.13-7.06 (m, 2H), 7.04 (s, 1H), 7.03-6.97 (m, 2H), 6.96 (s, 1H), 6.55 (d, J=4.5 Hz, 1H), 3.64-3.54 (m, 1H), 3.45 (dt, J=9.8, 6.3 Hz, 1H), 2.97 (dd, J=9.8, 8.2 Hz, 1H), 2.66 (d, J=12.6 Hz, 1H), 2.38 (s, 3H), 2.30-2.13 (m, 6H), 1.68 (dt, J=13.0, 6.7 Hz, 1H), 1.38 (s, 3H), 1.32 (s, 3H), 1.29 (s, 3H), 1.08 (s, 3H), 0.87 (d, J=6.8 Hz, 3H), 0.77 (d, J=6.8 Hz, 3H).

According to the above experimental process, a single chiral ligand $(R_a, S)$-I-c was obtained with a total yield of 90% by replacing the compound V with a chiral compound (R)-V.

According to the above experimental process, different chiral amino alcohols are employed to prepare the following chiral phosphinooxazoline ligand compounds:

(S)-2-((R)-7'-(diphenylphosphanyl)-3,3,3',3',5,5'-hexamethyl-2,2',3,3'-tetrahydro-1,1'-spirobi[inden]-7-yl)-4-phenyl-4,5-dihydrooxazole ((R$_a$, S)-I-2.11b)

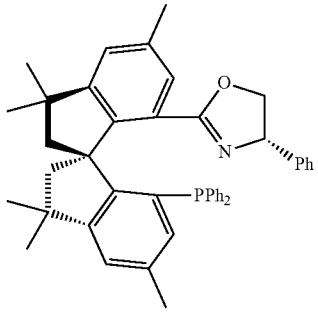

250 mg, a total two-step yield of 79%; white solid, m.p. 67-68° C.; $[\alpha]_D^{20}$=+74 (c 0.1, CH$_2$Cl$_2$); $^1$H NMR (400 MHz, CDCl$_3$) δ 7.57 (s, 1H), 7.24-7.19 (m, 3H), 7.13-6.94 (m, 11H), 6.90 (s, 1H), 6.73 (dd, J=8.0, 6.8 Hz, 3H), 4.83 (t, J=10.5 Hz, 1H), 4.21 (dd, J=9.9, 8.3 Hz, 1H), 3.14-2.87 (m, 2H), 2.41 (s, 3H), 2.27 (d, J=12.7 Hz, 2H), 2.19 (d, J=13.6 Hz, 1H), 2.08 (s, 3H), 1.37 (s, 3H), 1.32 (s, 3H), 1.30 (s, 3H), 1.13 (s, 3H);

(S)-2-((S)-7'-(diphenylphosphanyl)-3,3,3',3',5,5'-hexamethyl-2,2',3,3'-tetrahydro-1,1'-spirobi[inden]-7-yl)-4-phenyl-4,5-dihydrooxazole ((S$_a$, S)-I-2.11b)

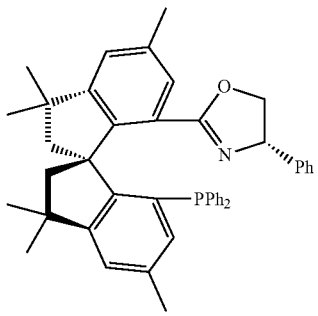

238 mg, a total two-step yield of 75%; white solid, m.p. 38-39° C.; $[\alpha]_D^{20}$=−138 (c 0.1, CH$_2$Cl$_2$); $^1$H NMR (400 MHz, CDCl$_3$) δ 7.59 (s, 1H), 7.30-7.08 (m, 12H), 7.07-6.95 (m, 4H), 6.94 (s, 1H), 6.63 (d, J=2.3 Hz, 1H), 4.90-4.56 (m, 1H), 3.82-3.65 (m, 1H), 3.42-3.30 (m, 1H), 2.84-2.70 (m, 1H), 2.40 (s, 3H), 2.33-2.16 (m, 6H), 1.33 (d, J=6.0 Hz, 6H), 1.26 (s, 3H), 1.15 (s, 3H);

(S)-4-benzyl-2-((R)-7'-(diphenylphosphanyl)-3,3,3',3',5,5'-hexamethyl-2,2',3,3'-tetrahydro-1,1'-spirobi[inden]-7-yl)-4,5-dihydrooxazole ((R$_a$, S)-I-2.11c)

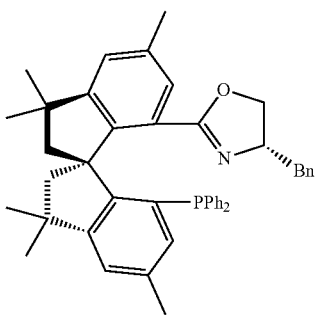

249 mg, a total two-step yield of 77%; white solid, m.p. 57-58° C.; $[\alpha]_D^{20}$=+106 (c 0.1, CH$_2$Cl$_2$); $^1$H NMR (400 MHz, CDCl$_3$) δ 7.46 (s, 1H), 7.23 (dd, J=7.0, 4.8 Hz, 5H), 7.17 (dd, J=7.4, 6.1 Hz, 6H), 7.07 (s, 1H), 6.97 (ddd, J=17.5, 11.6, 6.8 Hz, 5H), 6.64 (d, J=4.4 Hz, 1H), 4.10 (qd, J=9.3, 4.1 Hz, 1H), 3.75 (t, J=8.7 Hz, 1H), 3.04 (dd, J=13.7, 4.1 Hz, 1H), 2.89-2.71 (m, 2H), 2.41 (s, 3H), 2.25 (d, J=10.8 Hz, 4H), 2.20-2.06 (m, 2H), 1.73 (dd, J=13.6, 10.7 Hz, 1H), 1.37 (s, 3H), 1.31 (d, J=1.9 Hz, 6H), 1.08 (s, 3H);

(S)-benzyl-2-((S)-7'-(diphenylphosphanyl)-3,3,3',3',5,5'-hexamethyl-2,2',3,3'-tetrahydro-1,1'-spirobi[inden]-7-yl)-4,5-dihydrooxazole ((S$_a$, S)-I-2.11c)

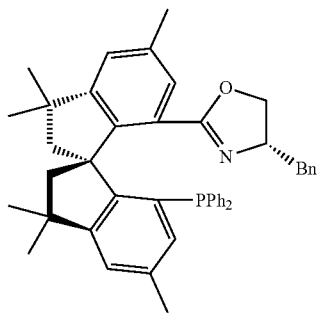

246 mg, a total two-step yield of 76%; white solid, m.p. 61-62° C.; $[\alpha]_D^{20}$=−125 (c 0.1, CH$_2$Cl$_2$); $^1$H NMR (400 MHz, CDCl$_3$) δ 7.42 (s, 1H), 7.29-7.23 (m, 2H), 7.23-7.14 (m, 7H), 7.07 (dd, J=10.4, 3.3 Hz, 5H), 7.01-6.95 (m, 2H), 6.92 (s, 1H), 6.59 (d, J=3.9 Hz, 1H), 4.05-3.91 (m, 1H), 3.52 (dd, J=8.3, 6.2 Hz, 1H), 3.12 (t, J=8.8 Hz, 1H), 2.87 (dd, J=13.9, 4.3 Hz, 1H), 2.75 (d, J=12.5 Hz, 1H), 2.39 (s, 3H), 2.29-2.17 (m, 3H), 2.15 (s, 3H), 2.04 (dd, J=13.8, 10.2 Hz, 1H), 1.39 (s, 3H), 1.33 (s, 3H), 1.30 (s, 3H), 1.13 (s, 3H);

(4S,5S)-2-((R)-7'-(diphenylphosphanyl)-3,3,3',3',5,5'-hexamethyl-2,2',3,3'-tetrahydro-1,1'-spirobi[inden]-7-yl)-4,5-diphenyl-4,5-dihydrooxazol ((R$_a$, S, S)-I-2.11d)

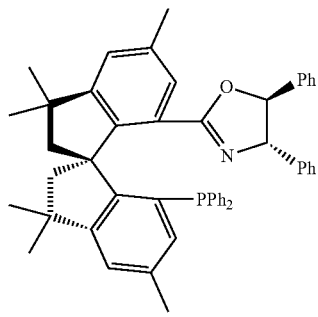

259 mg, a total two-step yield of 73%; white solid, m.p. 213-214° C.; $[\alpha]_D^{20}$=+94 (c 0.1, CH$_2$C$_2$); H NMR (400 MHz, CDCl$_3$) δ 7.71 (s, 1H), 7.25-7.18 (m, 6H), 7.11 (ddd, J=12.0, 7.4, 4.6 Hz, 5H), 7.05-6.90 (m, 8H), 6.87 (s, 1H), 6.81 (d, J=4.5 Hz, 1H), 6.64 (s, 1H), 6.62 (s, 1H), 4.62 (d, J=10.5 Hz, 1H), 4.14 (d, J=10.5 Hz, 1H), 3.03 (d, J=12.4 Hz, 1H), 2.45 (s, 3H), 2.29-2.16 (m, 3H), 2.10 (s, 3H), 1.33 (s, 3H), 1.22 (s, 3H), 1.13 (s, 3H), 1.00 (s, 3H);

(4,5S)-2-((S)-7'-(diphenylphosphanyl)-3,3,3',3'5,5'-hexamethyl-2,2',3,3'-tetrahydro-1,1'-spirobi[inden]-7-yl)-4,5-diphenyl-4,5-dihydrooxazole ((S$_a$, S, S)-I-2.11d)

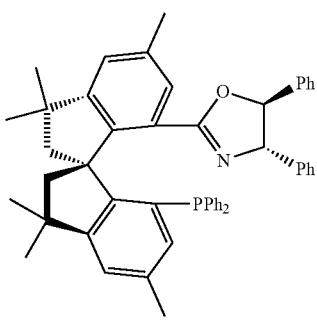

256 mg, a total two-step yield of 72%; white solid, m.p. 167-168° C.; $[\alpha]_D^{20}$=−43 (c 0.1, CH$_2$Cl$_2$); $^1$H NMR (400 MHz, CDCl$_3$) δ 7.54 (d, J=0.9 Hz, 1H), 7.25-7.05 (m, 15H), 6.97 (ddd, J=11.2, 7.9, 2.8 Hz, 4H), 6.77-6.53 (m, 4H), 4.85 (d, J=9.8 Hz, 1), 4.67 (d, J=9.8 Hz, 1H), 2.90 (d, J=12.5 Hz, 1H), 2.56 (d, J=12.9 Hz, 1H), 2.41 (d, J=12.4 Hz, 4), 2.18 (d, J=12.5 Hz, 1H), 2.07 (s, 3H), 1.32 (d, J=11.3 Hz, 9H), 1.13 (s, 3H).

The single crystals were obtained by cultivation in isopropyl ether, and the results of X-ray diffraction analysis are as follows:

The structure is shown in FIG. 1, and the data of crystal cell are as follows:

Bond precision: C—C=0.0074 A Wavelength=1.54184

Cell: a=11.6873(3)b=15.3134(3)c=14.6013(4)

alpha-90 beta=110.631(3) gamma=90

Temperature: 293 K

|  | Calculated | Reported |
|---|---|---|
| Volume | 2445.64(11) | 2445.63(10) |
| Space group | P 21 | P 1 21 1 |
| Hall group | P 2yb | P 2yb |
| Moiety formula | 2(C50 H48 N O P), C6 H14 O | 2(C50 H48 N O P), C6 H14 O |

Example 6

Application in Catalysts by Complexing with Metal Salts:

A metal salt Cu(OTf)$_2$ (0.005 mmol) and the ligand (R$_a$, S)-I-2.11c (0.005 mmol) were added to a Schlenk tube under N$_2$ protection. 1 ml of TFE (2,2,2-trifluoroethanol) was added and dissolved with stirring. The reaction was carried out under stirring at 50° C. for 60 min. Then, the solvent was removed under reduced pressure, and a quantitative metal complex [(R$_a$, S)-I-2.11c]Cu(OTf)$_2$ was obtained after vacuum drying.

Example 7

Application in Nickel-Assymetric Calculation of Sulfonamides

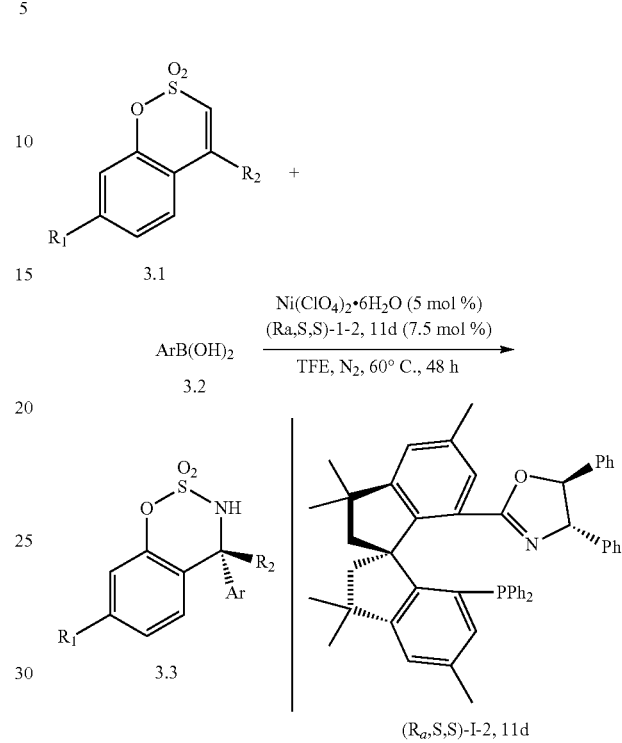

A metal salt Ni(ClO$_4$)$_2$.6H$_2$O (0.005 mmol) and the ligand (Ra, S, S)-I-2.11d (0.0075 mmol) were added to a Schlenk tube under N$_2$ protection. 0.5 ml of TFE (2,2,2-trifluoroethanol) was added and dissolved under stirring, and a coordination reaction was carried out at 60° C. for 30 min. Subsequently, benzo[e][1,2,3]oxthiazine-2,2-dioxide derivative 3.1(0.1 mmol), arylboronic acid 3.2 (0.15 mmol) and 0.5 ml of a solvent TFE were added. Then, the reaction was carried out at 60° C. for 48 h. After the reaction is completed, the reaction solution was directly subjected to silica gel column chromatography (eluent: ethyl acetate/petroleum ether=1/20-1/8) to obtain a chiral product 33.

The Results of Reactions are as Follows:

(R)-4-phenyl-3,4-dihydrobenzo[e][1,2,3]oxathiazine-2,2-dioxide (3.3a)

23 mg, yield: 88%; m.p. 131-132° C.; 99% ee; HPLC analysis: Chiralpak IC-3 (hexane/i-PrOH=90/10, 220 nm, 1.0 mL/min), t$_R$ (major) 10.2 min, t$_R$ (minor) 11.7 min; $[\alpha]_D^{20}$=+28.2 (c 0.10, CH$_2$Cl$_2$); $^1$H NMR (400 MHz, CDCl₃) δ 7.44 (dd, J=6.5, 3.7 Hz, 3H), 7.39-7.29 (m, 3H), 7.10 (t, J=7.7 Hz, 2H), 6.83 (d, J=7.6 Hz, 1H), 5.91 (s, 1H), 4.70 (s, 1H);

(R)-4-(m-tolyl)-3,4-dihydrobenzo[e][1,2,3]oxathiazine-2,2-dioxide (3.3b)

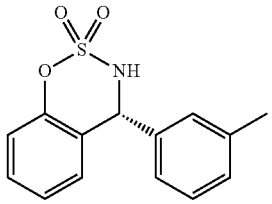 [SMILES: Cc1cccc([C@H]2NS(=O)(=O)Oc3ccccc32)c1]

25 mg, yield: 91%; m.p. 83-84° C.; 99% ee; HPLC analysis: Chiralpak IC-3 (hexane/i-PrOH=95/5, 220 nm, 1.0 mL/min), $t_R$ (major) 15.0 min, $t_R$ (minor) 17.4 min; $[\alpha]_D^{20}$=+12.1 (c 0.31, CH₂Cl₂); ¹H NMR (400 MHz, CDCl₃) δ 7.32 (dd, J=12.2, 4.8 Hz, 2H), 7.27-7.20 (m, 1H), 7.09 (ddd, J=15.0, 10.9, 2.6 Hz, 4H), 6.82 (d, J=7.8 Hz, 1H), 5.85 (s, 1H), 4.72 (s, 1H), 2.37 (s, 3H);

(R)-4-(p-tolyl)-3,4-dihydrobenzo[e][1,2,3]oxathiazine-2,2-dioxide (3.3c)

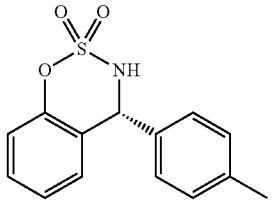 [SMILES: Cc1ccc([C@H]2NS(=O)(=O)Oc3ccccc32)cc1]

24 mg, yield: 87%; m.p. 120-121° C.; 93% ee; HPLC analysis: Chiralpak IC-3 (hexane/i-PrOH=95/5, 220 nm, 1.0 mL/min), $t_R$ (major) 16.0 min, ta (minor) 17.4 min; $[\alpha]_D^{20}$=+18.7 (c 0.12, CH₂Cl₂); ¹H NMR (400 MHz, CDCl₃) δ 7.31 (t, J=7.7 Hz, 1H), 7.27-7.17 (m, 4H), 7.07 (dd, J=15.6, 8.0 Hz, 2H), 6.82 (d, J=7.8 Hz, 1H), 5.86 (s, 1H), 4.73 (s, 1H), 2.38 (s, 3H);

(R)-4-([1,1'-biphenyl]-4-yl)-3,4-dihydrobenzo[e][1,2,3]oxathiazine-2,2-dioxide (3.3d)

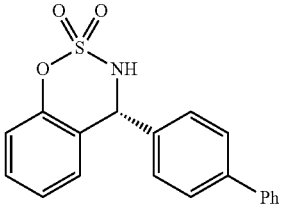 [SMILES: O=S1(=O)N[C@H](c2ccc(-c3ccccc3)cc2)c2ccccc2O1]

31 mg, yield: 92%; m.p. 167-168° C.; 99% ee; HPLC analysis: Chiralpak IC-3 (hexane/i-PrOH=90/10, 220 nm, 1.0 mL/min), $t_R$ (major) 12.5 min, $t_R$ (minor) 14.4 min; $[\alpha]_D^{20}$=+17.0 (c 0.10, CH₂C₂); ¹H NMR (400 MHz, CDCl₃) δ 7.64 (d, J=8.2 Hz, 2H), 7.62-7.54 (m, 2H), 7.46 (dd, J=10.3, 4.7 Hz, 2H), 7.38 (ddd, J=24.0, 11.4, 6.0 Hz, 4H), 7.10 (dd, J=14.8, 7.9 Hz, 2H), 6.89 (d, J=7.7 Hz, 1H), 5.95 (d, J=8.5 Hz, 1H), 4.77 (d, J=8.4 Hz, 1H);

(S)-4-(2-chlorophenyl)-3,4-dihydrobenzo[e][1,2,3]oxathiazine-2,2-dioxide (3.3e)

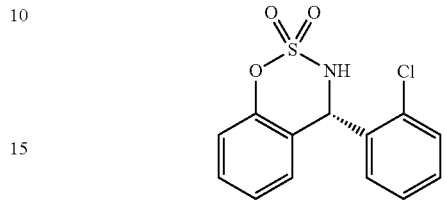

15 mg, yield: 51%; m.p. 114-115° C.; 93% ee; HPLC analysis: Chiralpak IF-3 (hexane/i-PrOH=90/10, 220 nm, 1.0 mL/min), $t_R$ (major) 6.2 min, $t_R$ (minor) 7.6 min; $[\alpha]_D^{20}$=+29.8 (c 0.08, CH₂Cl₂); ¹H NMR (400 MHz, CDCl₃) δ 7.51-7.45 (m, 1H), 7.44-7.29 (m, 4H), 7.15-7.05 (m, 2H), 6.78 (d, J=7.7 Hz, 1H), 6.30 (s, 1H), 5.09 (s, 1H);

(R)-4-(3-chlorophenyl)-3,4-dihydrobenzo[e][1,2,3]oxathiazine-2,2-dioxide (3.3l)

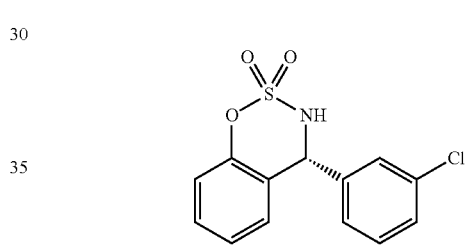

27 mg, yield: 91%; m.p. 104-105° C.; 99% ee; HPLC analysis: Chiralpak IC-3 (hexane/i-PrOH=95/5, 220 nm, 1.0 mL/min), $t_R$ (minor) 8.8 min, $t_R$ (major) 11.5 min; $[\alpha]_D^{20}$=+16.6 (c 0.28, CH₂C₂); ¹H NMR (400 MHz, CDCl₃) δ 7.45-7.32 (m, 4H), 7.28-7.23 (m, 1H), 7.11 (ddd, J=23.4, 11.7, 4.6 Hz, 2H), 6.83 (d, J=7.8 Hz, 1H), 5.87 (s, 1H), 4.79 (s, 1H);

(R)-4-(4-chlorophenyl)-3,4-dihydrobenzo[e][1,2,3]oxathiazine-2,2-dioxide (3.3 g)

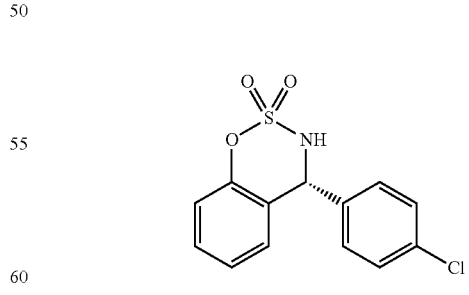

28 mg, yield: 93%; m.p. 139-140° C.; 99% ee; HPLC analysis: ChiralpakIC-3 (hexane/i-PrOH=90/10,220 nm, 1.0 mL/min), $t_R$ (major) 7.3 min, $t_R$ (minor) 9.8 min; $[\alpha]_D^{20}$=+8.5 (c 0.20, CH₂Cl₂); ¹H NMR (400 MHz, CDCl₃) δ 7.45-7.27 (m, 5H), 7.15-7.03 (m, 2H), 6.80 (d, J=7.8 Hz, 1H), 5.88 (d, J=8.4 Hz, 1H), 4.86 (d, J=8.3 Hz, 1H);

(R)-4(4-(trifluoromethyl)phenyl)-3,4-dihydrobenzo[e][1,2,3]oxathiazin-2,2-dioxide (3.3h)

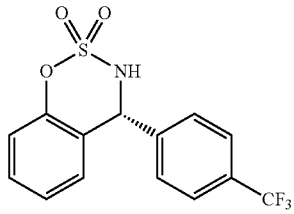 [SMILES: O=S1(=O)N[C@H](c2ccc(C(F)(F)F)cc2)c2ccccc2O1]

25 mg, yield: 76%; m.p. 119-120° C.; 98% ee; HPLC analysis: Chiralpak IF-3 (hexane/i-PrOH=90/10, 220 nm, 0.8 mL/min), $t_R$ (minor) 5.9 min, $t_R$ (major) 6.8 min; $[\alpha]_D^{20}$=+34.3 (c 0.07, $CH_2Cl_2$); $^1H$ NMR (400 MHz, $CDCl_3$) δ 7.64 (d, J=8.2 Hz, 2H), 7.43 (d, J=8.1 Hz, 2H), 7.30 (dd, J=11.5, 4.2 Hz, 1H), 7.12-7.00 (m, 2H), 6.73 (d, J=7.7 Hz, 1H), 5.91 (s, 1H), 4.72 (s, 1H);

(S)-4-(thiophen-3-yl)-3,4-dihydrobenzo[e][1,2,3]oxathiazine-2,2-dioxide (3.3i)

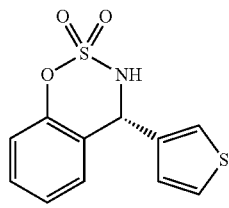 [SMILES: O=S1(=O)N[C@H](c2ccsc2)c2ccccc2O1]

22 mg, yield: 82%; white solid; m.p. 130-131° C.; 95% ee; HPLC analysis: Chiralpak IF-3 (hexane/i-PrOH=90/10, 220 nm, 0.8 mL/min), ta (minor) 9.9 min, $t_R$ (major) 12.9 min; $[\alpha]_D^{20}$=+59.2 (c 0.07, $CH_2Cl_2$); $^1H$ NMR (400 MHz, $CDCl_3$) δ 7.40 (ddd, J=4.3, 3.9, 2.3 Hz, 2H), 7.37-7.30 (m, 1H), 7.12 (td, J=7.7, 1.0 Hz, 1H), 7.05 (dd, J=8.3, 0.8 Hz, 1H), 7.01 (dd, J=4.9, 1.4 Hz, 1H), 6.94 (d, J=7.8 Hz, 1H), 6.04 (d, J=8.7 Hz, 1H), 4.79 (d, J=8.6 Hz, 1H);

(R)-4-(naphthalen-2-yl)-3,4-dihydrobenzo[e][1,2,3]oxathiazin-2,2-dioxide (3.3j)

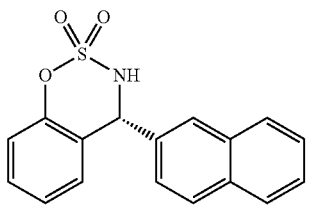 [SMILES: O=S1(=O)N[C@H](c2ccc3ccccc3c2)c2ccccc2O1]

28 mg, yield: 90%; m.p. 138-139° C.; 98% ee; HPLC analysis: Chiralpak IC-3 (hexane/i-PrOH=90/10, 1.0 mL/min), ta (major) 11.4 min, $t_R$ (minor) 18.3 min; $[\alpha]_D^{20}$=−48.3 (c 0.10, $CH_2Cl_2$); $^1H$ NMR (400 MHz, $CDCl_3$) δ 7.94-7.81 (m, 4H), 7.61-7.50 (m, 2H), 7.40-7.30 (m, 2H), 7.17-7.03 (m, 2H), 6.85 (d, J=7.8 Hz, 1H), 6.09 (d, J=11.3 Hz, 1H), 4.79 (s, 1H);

(R)-6-methyl-4-phenyl-3,4-dihydrobenzo[e][1,2,3]oxathiazine-2,2-dioxide (3.3k)

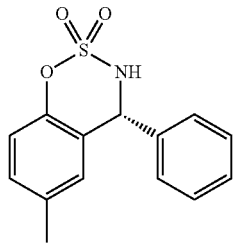 [SMILES: Cc1ccc2c(c1)[C@@H](c1ccccc1)NS(=O)(=O)O2]

26 mg, yield: 94%; m.p. 125-126° C.; 99% ee; HPLC analysis: Chiralpak IC-3 (hexane/i-PrOH=95/5, 220 nm, 1.0 mL/min), $t_R$ (major) 20.1 min, $t_R$ (minor) 21.9 min; $[\alpha]_D^{20}$=+57.0 (c 0.10, $CH_2C_2$); $^1H$ NMR (400 MHz, $CDCl_3$) δ 7.49-7.42 (m, 1H), 7.39-7.31 (m, 1H), 7.12 (dd, J=8.4, 1.9 Hz, 1H), 6.97 (d, J=8.4 Hz, 1H), 6.60 (s, 1H), 5.86 (s, 1H), 4.65 (s, 1H), 2.21 (s, 1H);

(R)-6-chloro-4-phenyl-3,4-dihydrobenzo[e][1,2,3]oxathiazine-2,2-dioxide (3.3l)

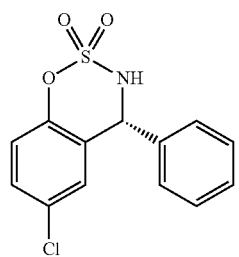 [SMILES: O=S1(=O)N[C@H](c2ccccc2)c2cc(Cl)ccc2O1]

26 mg, yield: 88%; m.p. 137-138° C.; 99% cc; HPLC analysis: Chiralpak IC-3 (hexane/i-PrOH=98/2, 220 nm, 0.8 mL/min), $t_R$ (major) 34.6 min, $t_R$ (minor) 40.7 min; $[\alpha]_D^{20}$=+33.9 (c 0.22, $CH_2Cl_2$); H NMR (400 MHz, $CDCl_3$) δ 7.46 (d, J=2.9 Hz, 3H), 7.38-7.28 (m, 3H), 7.04 (d, J=8.8 Hz, 1H), 6.81 (d, J=1.3 Hz, 1H), 5.86 (s, 1H), 4.71 (s, 1H).

Example 8

A metal salt $Ni(ClO_4)_2 \cdot 6H_2O$ (0.005 mmol) and the ligand ($S_a$, S)-I-2.11b (0.005 mmol) were added into a Schlenk tube under $N_2$ protection. Then, 0.5 ml of TFE (2,2,2-trifluoroethanol) was added and dissolved under stirring, and the reaction was carried out at 60° C. for 60 min. A metal complex [($S_a$, S)-I-2.11b]Ni(ClO$_4$)$_2$ was obtained after vacuum drying.

What is claimed is:

1. A 3,3,3',3'-tetramethyl-1,1'-spirobiindane-based phosphinooxazoline ligand, being a enantiomer or a diastereoisomer of a compound represented by formula I:

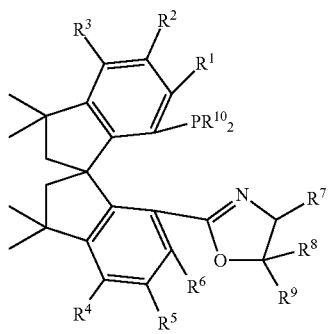

I wherein $R^1$ and $R^6$ are each independently selected from the group consisting of hydrogen, $C_1$-$C_{10}$ alkyl or perfluoroalkyl, $C_3$-$C_6$ cycloalkyl, and $C_1$-$C_4$ alkoxy or perfluoroalkoxy; $R^2$, $R^3$, $R^4$, and $R^5$ are each independently selected from the group consisting of hydrogen, halogen, $C_1$-$C_{10}$ alkyl or perfluoroalkyl, and $C_3$-$C_6$ cycloalkyl; $R^7$ is selected from the group consisting of hydrogen, $C_1$-$C_{10}$ alkyl or perfluoroalkyl, $C_3$-$C_6$ cycloalkyl, $C_6$-$C_{14}$ aryl, $CMe_2OBn$, $CMe_2Ph$, $CMePh_2$, $CPh_3$, $CH(Ph)OMe$, and $CH(Ph)OBn$; $R^8$ and $R^9$ are each independently selected from the group consisting of hydrogen, $C_1$-$C_{10}$ alkyl or perfluoroalkyl, $C_3$-$C_6$ cycloalkyl, $C_6$-$C_{14}$ aryl, $CH_2OCHPh_2$, $CH_2OCPh_3$, and $CH_2OCH_2Ph$; and $R^{10}$ is selected from the group consisting of $C_1$-$C_{10}$ alkyl or perfluoroalkyl, $C_3$-$C_6$ cycloalkyl, and $C_6$-$C_{14}$ aryl.

2. The 3,3,3',3'-tetramethyl-1,1'-spirobiindane-based phosphinooxazoline ligand according to claim 1, wherein the compound represented by formula I is any one of the following compounds:

($R_a$,S)-I-a

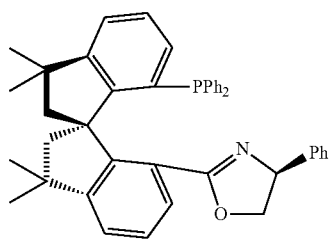

($S_a$,S,S)-I-b

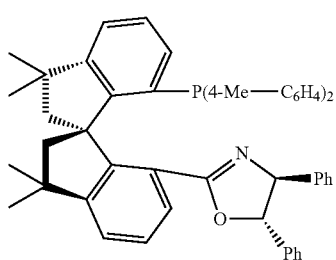

($R_a$,S)-I-c

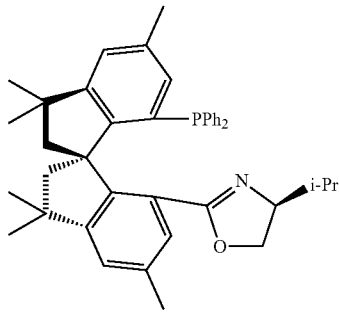

($S_a$,S)-I-d

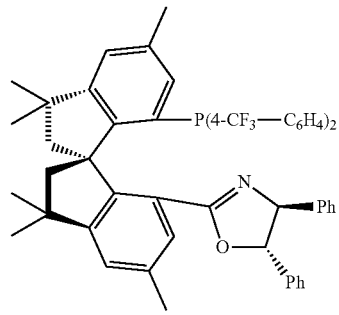

($R_a$,S)-I-e

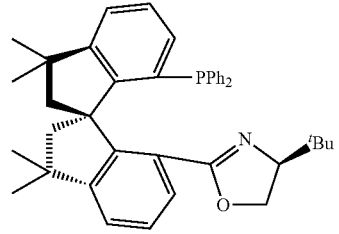

($S_a$)-I-f

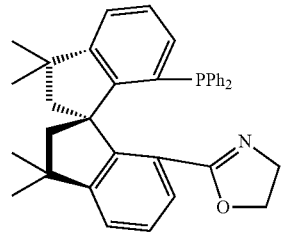

($R_a$,R)-I-g

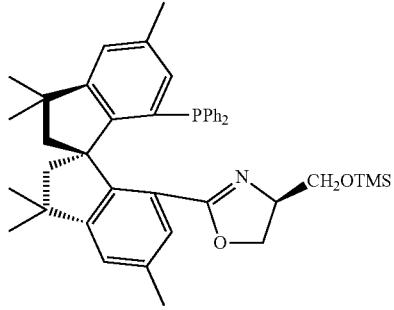

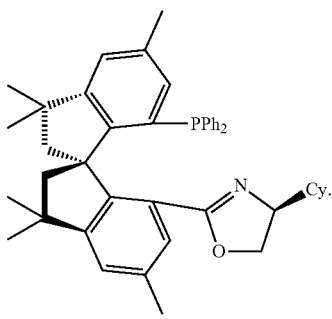

(S<sub>a</sub>,S)-I-h

3. A preparation method of the compound I according to claim 1, comprising the following steps:

preparing a compound represented by formula III through a mono-substitution reaction of a compound represented by formula II, as a starting material, with disubstituted phosphine halide under an effect of an alkali, subjecting the compound represented by formula III to a palladium-catalyzed cyanation, an acidic hydrolysis, and a condensation reaction with an aminoethanol compound to form amphenicol, and then conducting a cyclization reaction to obtain the compound represented by formula I, as the following reaction scheme:

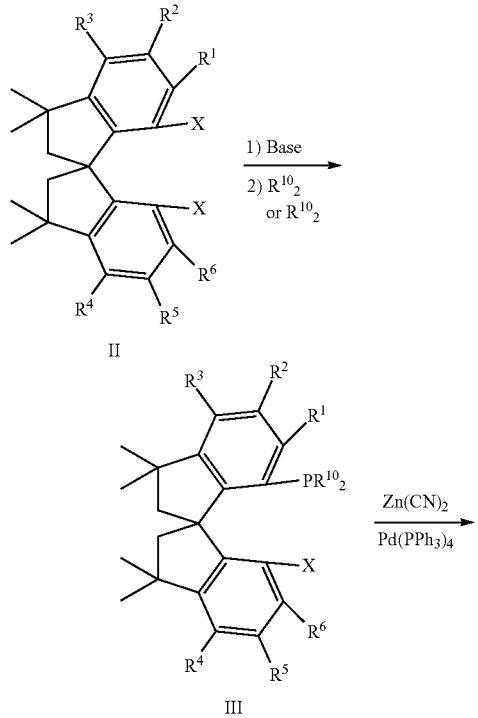

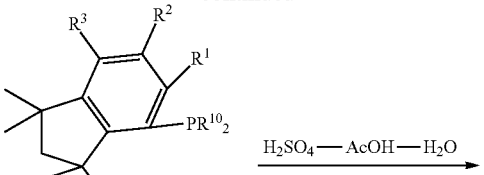

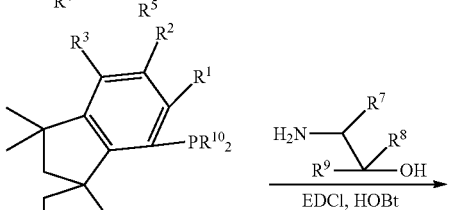

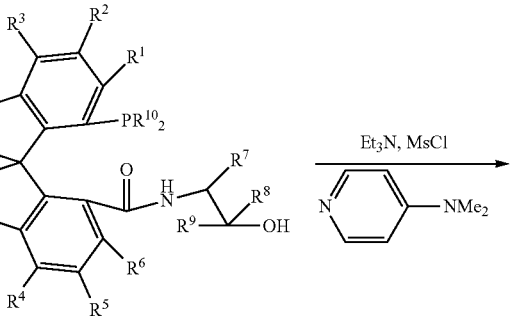

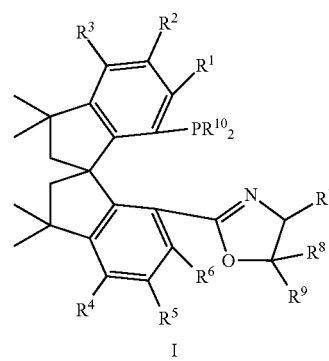

wherein $R^1$-$R^{10}$ in the formula I are the same as those defined in claim 1; X in the formula II is bromine or iodine; and wherein EDCI is 1-(3-dimethylaminopropyl)-3-ethylcarbodiimide hydrochloride, and HOBt is 1-hydroxybenzotriazole.

* * * * *